United States Patent
Trim et al.

(10) Patent No.: US 11,955,247 B2
(45) Date of Patent: Apr. 9, 2024

(54) MOBILE AUTOMATION CONTROL OF DISEASE SPREAD

(71) Applicant: INTERNATIONAL BUSINESS MACHINES CORPORATION, Armonk, NY (US)

(72) Inventors: Craig M. Trim, Ventura, CA (US); Sarbajit K. Rakshit, Kolkata (IN); Munish Goyal, Yorktown Heights, NY (US); Zachary A. Silverstein, Jacksonville, FL (US); Shikhar Kwatra, Durham, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 772 days.

(21) Appl. No.: 16/567,861

(22) Filed: Sep. 11, 2019

(65) Prior Publication Data
US 2021/0074436 A1 Mar. 11, 2021

(51) Int. Cl.
*G16H 50/80* (2018.01)
*A47L 11/40* (2006.01)
(Continued)

(52) U.S. Cl.
CPC .......... *G16H 50/80* (2018.01); *A47L 11/4011* (2013.01); *G06V 40/161* (2022.01);
(Continued)

(58) Field of Classification Search
CPC ............................... G16H 50/80; G16H 50/30
See application file for complete search history.

(56) References Cited

U.S. PATENT DOCUMENTS 7,485,095 B2 2/2009 Shusterman
10,362,769 B1 * 7/2019 Kartoun ................. G16H 50/70
(Continued)

FOREIGN PATENT DOCUMENTS

| CN | 101959449 | 1/2011 |
| KR | 20080107961 | 12/2008 |
| KR | 20180133064 | 12/2018 |

OTHER PUBLICATIONS

ARPO The Robot, "ARPO The Robot For All Kids—Evil Germs || Video For Kids" YouTube video, link: https://www.youtube.com/watch?v=iB9GPEdWaqo, Dec. 8, 2018, screenshots 1-5 (Year: 2018).*

(Continued)

*Primary Examiner* — Rajesh Khattar
*Assistant Examiner* — Steven G. S. Sanghera
(74) *Attorney, Agent, or Firm* — Nicholas Welling; Andrew D. Wright; Calderon Safran & Cole, P.C.

(57) ABSTRACT

Methods and systems for mobile automation control of disease spread are disclosed. A computer-implemented method includes: determining, by a computing device, a health status of a person; determining, by the computing device, that the person is sick based on the health status; determining, by the computing device, facial and body movements of the person determined to be sick; determining, by the computing device, that the person determined to be sick performed a germ-transmitting activity based on the facial and body movements; and deploying, by the computing device, a cleaning robot to clean based on the determining that the person determined to be sick performed the germ-transmitting activity.

20 Claims, 5 Drawing Sheets

(51) Int. Cl.
   *G06V 40/16* (2022.01)
   *G06V 40/20* (2022.01)
   *G16H 50/30* (2018.01)

(52) U.S. Cl.
   CPC .............. *G06V 40/23* (2022.01); *G16H 50/30* (2018.01); *A47L 2201/04* (2013.01); *A47L 2201/06* (2013.01)

(56) References Cited

U.S. PATENT DOCUMENTS

| | | |
|---|---|---|
| 2016/0132652 A1 | 5/2016 | Chapman Bates et al. |
| 2017/0043048 A1* | 2/2017 | Fang ........................ H01J 33/04 |
| 2017/0314961 A1* | 11/2017 | Chen ................... G06F 11/3072 |
| 2018/0068179 A1 | 3/2018 | Derenne et al. |
| 2018/0325385 A1* | 11/2018 | Deterding ............ A61B 5/0205 |
| 2019/0011923 A1 | 1/2019 | Xie |
| 2019/0252078 A1* | 8/2019 | Schubert ................ G16H 10/60 |
| 2020/0397341 A1* | 12/2020 | Tatavarti .............. A61B 5/0803 |

OTHER PUBLICATIONS

Clement Weiss, "Cleaning Robot Animation.wmv" YouTube video, link: https://www.youtube.com/watch?v=6hrVuVyT7JU, Jan. 6, 2011, screenshots 1-2 (Year: 2011).*

Mell et al., "The NIST Definition of Cloud Computing", NIST, Special Publication 800-145, Sep. 2011, 7 pages.

\* cited by examiner

MOBILE AUTOMATION CONTROL OF DISEASE SPREAD

BACKGROUND

The present invention generally relates to computing devices and, more particularly, to methods and systems for mobile automation control of disease spread.

Most cough, cold, and flu viruses are thought to be passed from person to person by contact with respiratory droplets. These respiratory droplets generally have a very short lifespan. However, environmental factors such as low temperature and moisture in the air may increase the lifespan of respiratory droplets and contribute to the spread of disease more than in a relatively dry condition. Detection and control of clumps of respiratory droplets may prevent the spread of disease within an enclosed environment.

IBM® (IBM is a registered trademark of International Business Machines Corporation in the United States and/or other countries) developed disease modeling with the Spatiotemporal Epidemiological Modeler (STEM). STEM includes capabilities to forecast and analyze the possible spread of infectious disease and simulate spread of disease across time and space. STEM allows epidemiologists, public health officials, and students to collaborate and share data and models for infectious diseases on a common platform. STEM uses large data sets on such things as airport and highway traffic and county infrastructures with a wide range of variables, such as the infectiousness of a disease and the availability and distribution of a vaccine. This allows epidemiologists, public health officials, and students to look at and understand different scenarios, get insight into what the impact of decisions might be and, in some cases, potentially prevent the spread of such diseases.

SUMMARY

In a first aspect of the invention, there is a computer-implemented method that includes: determining, by a computing device, a health status of a person; determining, by the computing device, that the person is sick based on the health status; determining, by the computing device, facial and body movements of the person determined to be sick; determining, by the computing device, that the person determined to be sick performed a germ-transmitting activity based on the facial and body movements; and deploying, by the computing device, a cleaning robot to clean based on the determining that the person determined to be sick performed the germ-transmitting activity.

In another aspect of the invention, there is a computer program product that includes a computer readable storage medium having program instructions embodied therewith. The program instructions are executable by a computing device to cause the computing device to: determine a health status of each of a plurality of persons in an enclosed area; determine that at least one of the plurality of persons is sick based on the health status; determine facial and body movements of the at least one of the plurality of persons determined to be sick; determine that the at least one of the plurality of persons determined to be sick performed a germ-transmitting activity based on the facial and body movements; and deploy a cleaning robot to clean based on the determining that the at least one of the plurality of persons determined to be sick performed the germ-transmitting activity.

In another aspect of the invention, there is a system that includes: a hardware processor, a computer readable memory, and a computer readable storage medium associated with a computing device; program instructions to determine a health status of a person; program instructions to determine that the person is sick based on the health status; program instructions to determine facial and body movements of the person determined to be sick; program instructions to determine that the person determined to be sick performed a germ-transmitting activity based on the facial and body movements; and program instructions to deploy a cleaning robot to clean based on the determining that the person determined to be sick performed the germ-transmitting activity, wherein the program instructions are stored on the computer readable storage medium for execution by the hardware processor via the computer readable memory

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION

The present invention generally relates to computing devices and, more particularly, to methods and systems for mobile automation control of disease spread. As described herein, aspects of the invention include a method and system for determining if a person is sick and, in response to determining that a person is sick, automatically taking steps to mitigate the spread of cough, cold, and flu viruses and other illnesses (e.g., by notifying the sick person of actions to take, activating a cleaning robot, and/or adjusting home features). Aspects of the invention also include a method and system for using computer vision and distance computation from proximal areas as well as health parameters in order to detect a level of disease spread and determine amelioration strategies to be deployed in order to lower a risk of disease spread. Aspects of the invention also include a home automation method and system that detects contours of spatiotemporal respiratory droplet clumps and advises persons of appropriate actions to take in order to prevent or control the spread of viral diseases in a home environment or other enclosed environment.

Embodiments address the problem of disease spread within an enclosed environment such as a home or office. Accordingly, embodiments improve the functioning of a computer by providing methods and systems for mobile automation control of disease spread. In particular, embodiments improve software by providing a method and system for determining if a person is sick and, in response to determining that a person is sick, automatically taking steps to mitigate the spread of cough, cold, and flu viruses and other illnesses. Embodiments also improve software by providing a method and system for using computer vision and distance computation from proximal areas as well as health parameters in order to detect a level of disease spread and determine amelioration strategies to be deployed in order to lower a risk of disease spread. Embodiments also improve software by providing a home automation method and system that detects contours of these spatiotemporal respiratory droplet clumps and advises persons of appropriate actions to take in order to prevent or control the spread of viral diseases in a home environment or other enclosed environment. Additionally, implementations of the invention use techniques that are, by definition, rooted in computer technology (e.g., artificial intelligence, machine learning, computer vision, neural networks, and cloud computing).

To the extent the implementations collect, store, or employ personal information (e.g., health-related information including biometric information) of individuals, it should be understood that such information shall be used in accordance with all applicable laws concerning protection of personal information. Additionally, the collection, storage, and use of such information, as well as, e.g., use of the mobile automation control of disease spread methods and systems described herein, may be subject to advance notification and consent of the individual to such activity, for example, through "opt-in" or "opt-out" processes as may be appropriate for the situation and type of information. Storage and use of personal information may be in an appropriately secure manner reflective of the type of information, for example, through various encryption and anonymization techniques for particularly sensitive information.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 1:
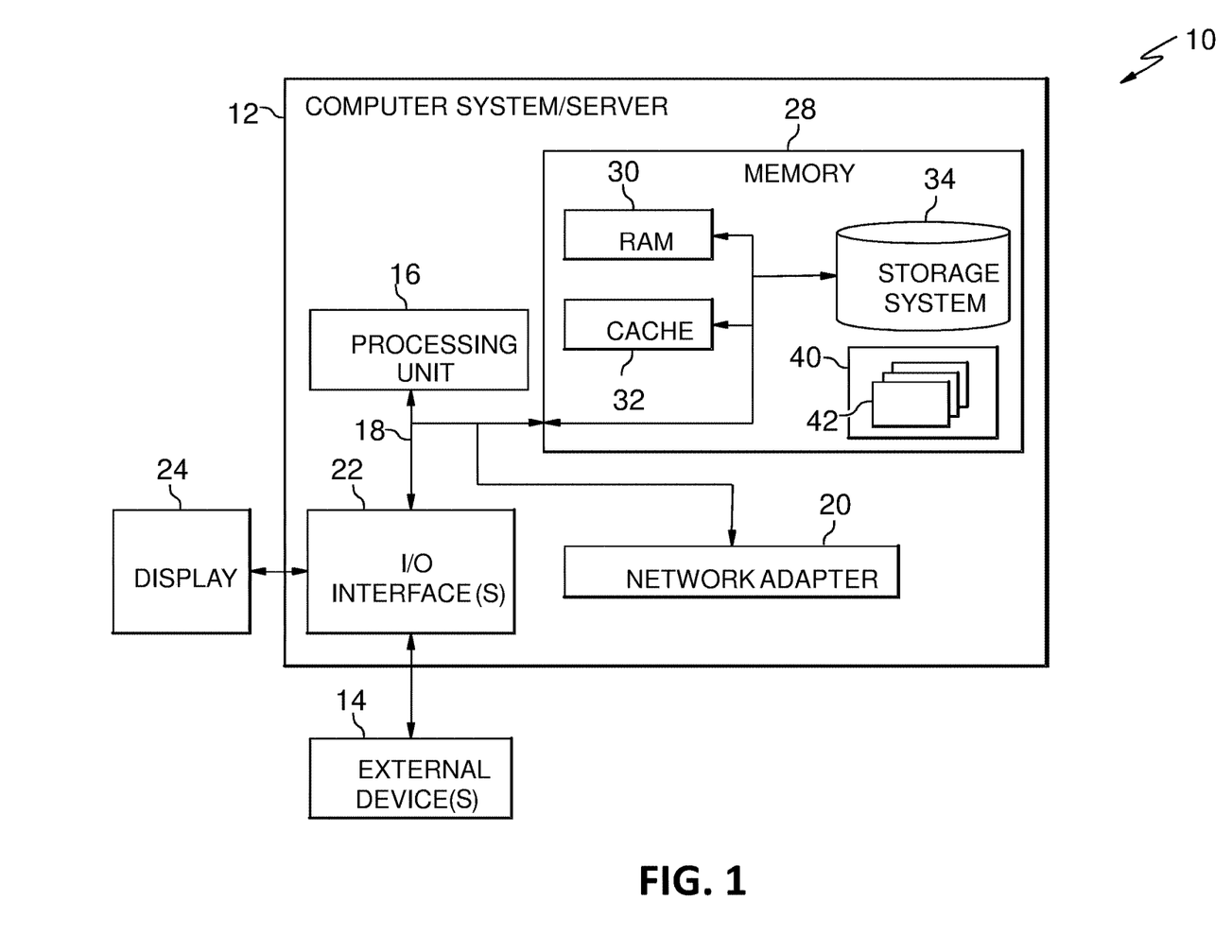
FIG. 1 depicts a cloud computing node according to an embodiment of the present invention.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
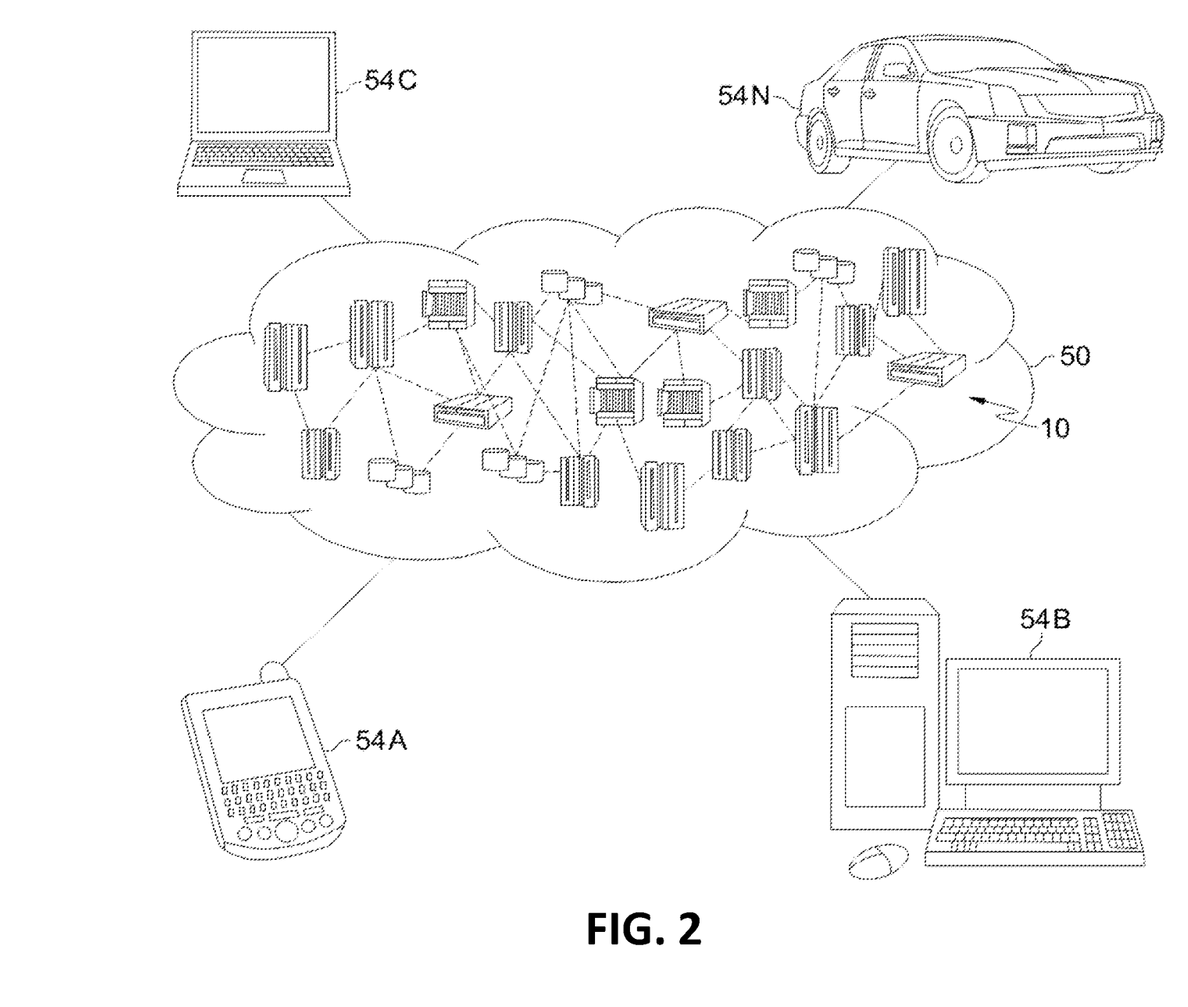
FIG. 2 depicts a cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
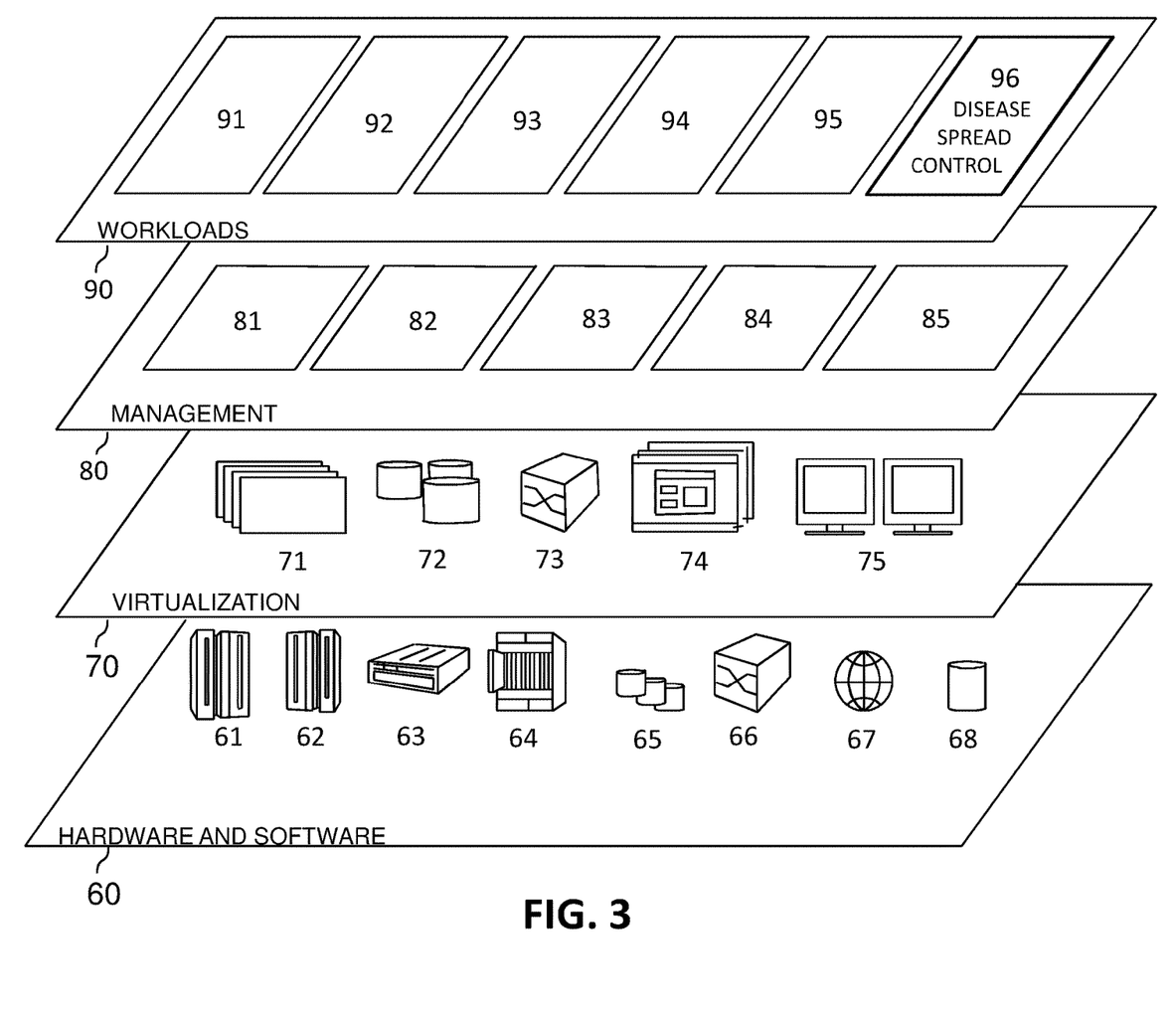
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and disease spread control 96.

Referring back to FIG. 1, the program/utility 40 may include one or more program modules 42 that generally carry out the functions and/or methodologies of embodiments of the invention as described herein (e.g., such as the functionality provided by disease spread control 96). Specifically, the program modules 42 may determine if a person is sick and, in response to determining that a person is sick, automatically take steps to mitigate the spread of cough, cold, and flu viruses and other illnesses. Additionally, the program modules 42 may use computer vision and distance computation from proximal areas as well as health parameters in order to detect a level of disease spread and determine amelioration strategies to be deployed in order to prevent a high-risk situation. Other functionalities of the program modules 42 are described further herein such that the program modules 42 are not limited to the functions described above. Moreover, it is noted that some of the modules 42 can be implemented within the infrastructure shown in FIGS. 1-3. For example, the modules 42 may be representative of a disease spread control program module 410 as shown in FIG. 4.

Figure 4:
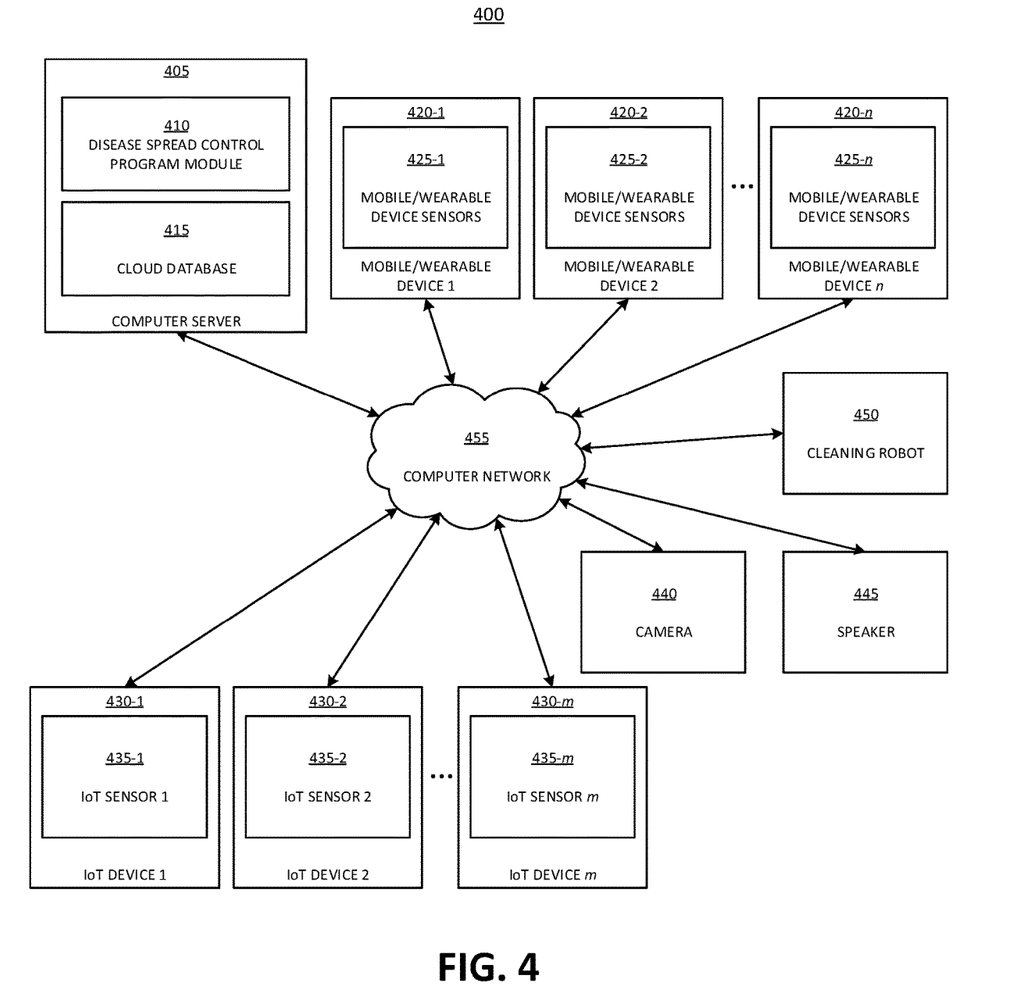
FIG. 4 depicts an illustrative environment in accordance with aspects of the invention.

FIG. 4 depicts an illustrative environment 400 in accordance with aspects of the invention. As shown, the environment 400 comprises a computer server 405, a plurality of mobile/wearable devices 420-1, 420-2, . . . , 420-n, a plurality of Internet of Things (IoT) devices 430-1, 430-2, . . . , 430-m, at least one camera 440, at least one speaker 445, and at least one cleaning robot 450, which are in communication via a computer network 455. In embodiments, the computer network 455 is any suitable network including any combination of a LAN, WAN, or the Internet. In embodiments, one or more of the computer server 405, the plurality of mobile/wearable devices 420-1, 420-2, . . . , 420-n, the plurality of Internet of Things (IoT) devices 430-1, 430-2, . . . , 430-m, the at least one camera 440, the at least one speaker 445, and the at least one cleaning robot 450 are physically collocated and/or are situated in separate physical locations.

The quantity of devices and/or networks in the environment 400 is not limited to what is shown in FIG. 4. In practice, the environment 400 may include additional devices and/or networks; fewer devices and/or networks; different devices and/or networks; or differently arranged devices and/or networks than illustrated in FIG. 4. Also, in some implementations, one or more of the devices of the environment 400 may perform one or more functions described as being performed by another one or more of the devices of the environment 400.

In embodiments, the computer server 405 is a cloud computing node 10 (as shown in FIG. 1). In embodiments, the computer server 405 may be implemented as hardware and/or software using components such as mainframes 61; RISC (Reduced Instruction Set Computer) architecture based servers 62; servers 63; blade servers 64; storage devices 65; networks and networking components 66; virtual servers 71; virtual storage 72; virtual networks 73, including virtual private networks; virtual applications and operating systems 74; and virtual clients 75 shown in FIG. 3.

In embodiments, the computer server 405 includes disease spread control program module 410 which provides for mobile automation control of disease spread. In embodiments, the program instructions included in the disease spread control program module 410 of the computer server 405 are executed by one or more hardware processors. In embodiments, the computer server 405 also includes cloud database 415, which stores historical health-related information for a plurality of persons, as described below.

Still referring to FIG. 4, in embodiments, each of the plurality of mobile/wearable devices 420-1, 420-2, . . . , 420-n is any type of mobile device, mobile telephone, computer-based activity tracker, fitness tracker, smart watch, sleep tracker, biosensor device, or other device that is typically carried or worn by a user and that tracks information related to activity, fitness, location, and/or health. In embodiments, each of the plurality of mobile/wearable devices 420-1, 420-2, . . . , 420-n includes one or more elements of the computer system/server 12 (as shown in FIG. 1). Each of the plurality of mobile/wearable devices 420-1, 420-2, . . . , 420-n includes at least one mobile/wearable device sensor 425-1, 425-2, . . . , 425-n that collects biometric data (e.g., heart rate) and/or data that is related to activity, fitness, location, and/or health.

Still referring to FIG. 4, in embodiments, each of the plurality of IoT devices 430-1, 430-2, . . . , 430-m is any type of computer-based device (e.g., a smart home device) that includes at least one IoT sensor 435-1, 435-2, 435-m such as digital video cameras, digital still cameras, microphones, temperature sensors, motion sensors, location sensors, and any other type of digital sensor that collects data in a user's home, workplace, or any other location where each of the plurality of IoT devices 430-1, 430-2, . . . , 430-m is present. In embodiments, each of the plurality of IoT devices 430-1, 430-2, . . . , 430-m includes one or more elements of the computer system/server 12 (as shown in FIG. 1).

Still referring to FIG. 4, in embodiments, the at least one camera 440 is a network-connected digital still camera or a network-connected digital video camera (e.g., an Internet Protocol camera). In embodiments, the at least one camera 440 includes a charge-coupled device (CCD) sensor or a complementary metal-oxide-semiconductor (CMOS) sensor and transmits digital still images and/or digital video (optionally including audio) via the computer network 455.

Still referring to FIG. 4, in embodiments, the at least one speaker 445 is a network-connected speaker (e.g., a smart speaker). In embodiments, the at least one speaker 445 plays back audio received via the computer network 455 (e.g., in response to a command from the disease spread control program module 410 of the computer server 405). Additionally, in embodiments, the at least one speaker 445 includes an integrated virtual assistant that may interpret and respond to audio commands issued by a user.

Still referring to FIG. 4, in embodiments, the at least one cleaning robot 450 is a network-connected cleaning robot such as a floor cleaning robot (e.g., vacuuming robot, sweeping robot, or mopping robot), surface cleaning robot, window cleaning robot, air purifying robot, or any other type of cleaning robot. In embodiments, the at least one cleaning robot 450 uses artificial intelligence techniques to autonomously or semi-autonomously clean a target area in response to a command received via the computer network 455 (e.g., from the disease spread control program module 410 of the computer server 405).

Figure 5:
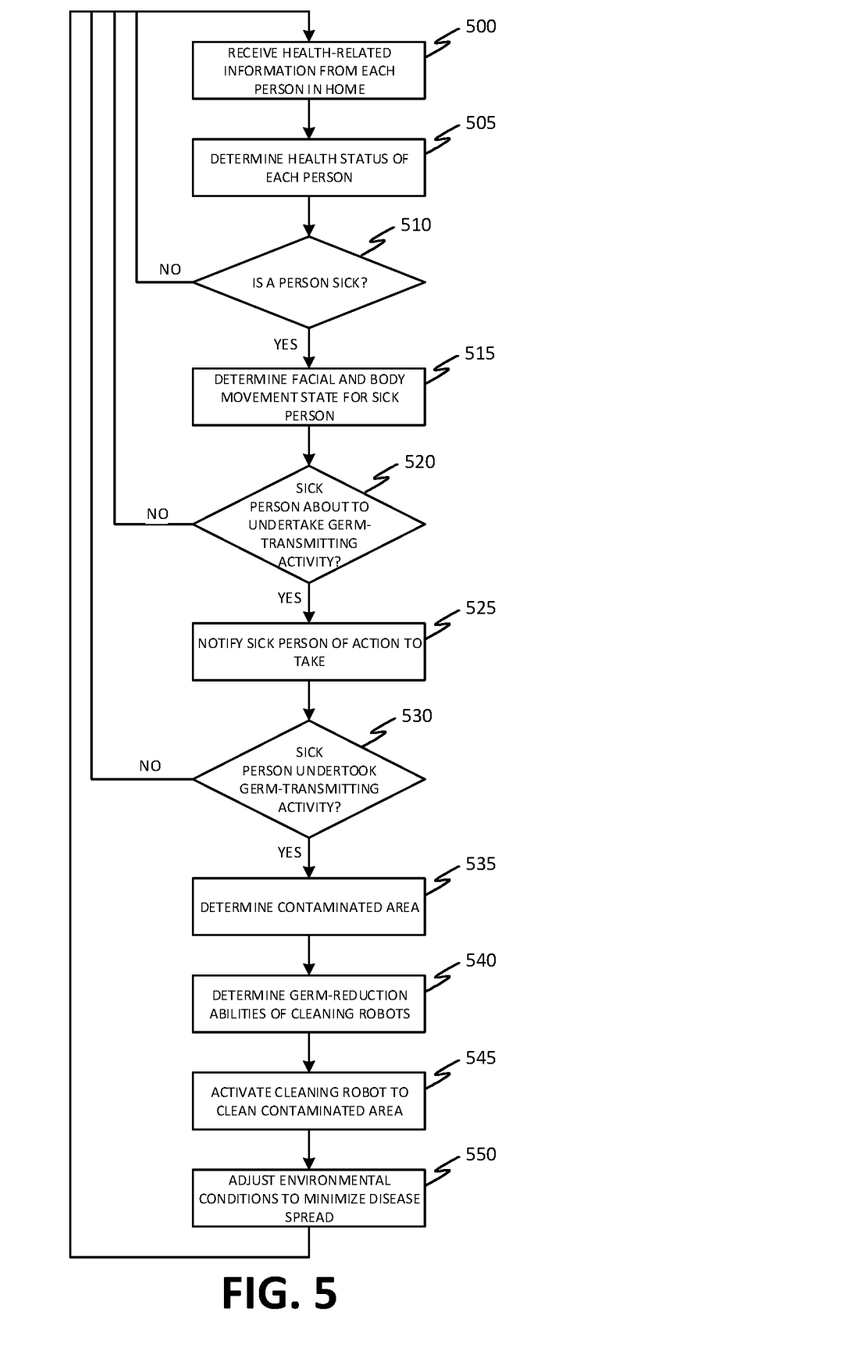
FIG. 5 depicts a flowchart of an exemplary method performed in accordance with aspects of the invention.

FIG. 5 depicts a flowchart of an exemplary method performed by the disease spread control program module 410 of the computer server 405 in accordance with aspects of the invention. The steps of the method are performed in the environment of FIG. 4 and are described with reference to the elements shown in FIG. 4.

At step 500, the computer server 405 receives health-related information from each person in a home. In embodiments, the disease spread control program module 410 receives health-related information from each of a plurality of persons in a home, office, or other enclosed environment. In embodiments, the health-related information received by the disease spread control program module 410 may include biometric information (e.g., heartrate, temperature, etc.) or other health-related information sensed or otherwise collected by one or more of the mobile/wearable device sensors 425-1, 425-2, . . . , 425-*n* of one or more of the mobile/wearable devices 420-1, 420-2, . . . , 420-*n*. In embodiments, the health-related information received by the disease spread control program module 410 may also include biometric information or other health-related information sensed or otherwise collected by one or more of the IoT sensors 435-1, 435-2, . . . , 435-*m* of one or more of the IoT devices 430-1, 430-2, . . . , 430-*m*. In embodiments, the disease spread control program module 410 stores the received health-related information (or a summary thereof) from each of the plurality of persons in the home, office, or other enclosed environment in the cloud database 415 to build a profile over time of historical health-related information for each person.

Still referring to FIG. 5, at step 505, the computer server 405 determines a health status of each person. In embodiments, for each person in the home, office, or other enclosed environment, the disease spread control program module 410 uses the health-related information received at step 500 and the profile of historical health-related information for the person stored in the cloud database 415 to determine the health status (e.g., well or sick) of the person. In particular, the disease spread control program module 410 analyzes the profile of historical health-related information for the person stored in the cloud database 415 and determines whether or not the health-related information received at step 500 for a current time period deviates from the health-related information in the profile. In embodiments, the disease spread control program module 410 also analyzes visual data (e.g., using computer vision techniques and convolutional neural networks) including digital still images and/or digital video of the person from the at least one camera 440 to determine the health status.

Still referring to step 505, in embodiments, if the disease spread control program module 410 determines that one or more items of health-related information received at step 500 deviate from the profile in the cloud database 415 by more than a threshold amount (e.g., a person's body temperature is more than 1.5 degrees higher than a baseline body temperature indicated by the profile), then the disease spread control program module 410 determines the health status of the person is sick. On the other hand, if the disease spread control program module 410 determines that no items of health-related information received at step 500 deviate from the profile in the cloud database by more than the threshold amount, then the then disease spread control program module 410 determines the health status of the person is well. In other embodiments, the health status determined by the disease spread control program module 410 indicates a probability that the person is sick, determined based on an amount of deviation between the health-related information received at step 500 and the profile in the cloud database 415.

Still referring to FIG. 5, at step 510, the computer server 405 determines whether or not a person is sick. In embodiments, the disease spread control program module 410 determines whether a person in the home, office, or other enclosed environment is sick based on the health statuses determined at step 505. If the disease spread control program module 410 determines that at least one person is sick (e.g., the health status of a person is sick, or the health status indicates that a person is sick with a probability that exceeds a threshold), then the flow proceeds to step 515. On the other hand, if the disease spread control program module 410 determines that it is not the case that a person is sick, then the flow returns to step 500.

Still referring to FIG. 5, at step 515, the computer server 405 determines a facial and body movement state for the sick person. In embodiments, the disease spread control program module 410 determines the facial and body movement state for the sick person. In particular, for each person having a health status of sick (as determined at step 505), the disease spread control program module 410 receives digital still images and/or digital video of the person from the at least one camera 440. The disease spread control program module 410 analyzes the received digital still images and/or digital video using computer vision techniques and convolutional neural networks to determine the facial and body movement state for the sick person. In an example, the disease spread control program module 410 determines movements of facial muscles that may indicate that the sick person is about to sneeze and/or determines a body movement that may indicate that the sick person is about to touch a surface such as a doorknob or light switch.

Still referring to FIG. 5, at step 520, the computer server 405 determines whether or not a sick person is about to undertake a germ-transmitting activity. In embodiments, the disease spread control program module 410 uses the facial and body movement state determined at step 515 to determine whether or not the sick person is about to undertake a germ-transmitting activity. In particular, for each person having a health status of sick (as determined at step 505), the disease spread control program module 410 determines if the facial and body movement state determined at step 515 indicates that the person is about to sneeze/cough, about to touch a surface such as a doorknob or light switch, or about to undertake any other germ-transmitting activity.

Still referring to step 520, if the disease spread control program module 410 determines that the facial and body movement state indicates that that the person is about to sneeze/cough, about to touch a surface such as a doorknob or light switch, or about to undertake any other germ-transmitting activity, then the flow proceeds to step 525. On the other hand, if the disease spread control program module 410 determines that the facial and body movement state does not indicate that that the person is about to sneeze/cough, about to touch a surface such as a doorknob or light switch, or about to undertake any other germ-transmitting activity, then the flow returns to step 500.

Still referring to FIG. 5, at step 525, the computer server 405 notifies a sick person of an action to take. In embodiments, the disease spread control program module 410 notifies the sick person of the action to take. In particular, the disease spread control program module 410 sends a voice-based alert to the sick person via the at least one speaker 445. In embodiments, the voice-based alert is a reminder to the sick person to take an action to avoid or mitigate the germ-transmitting activity. In an example, if the disease spread control program module 410 determines at step 520 that the facial and body movement state indicates that a user is about to undertake an action that may contribute to the spread of a contagion, then the disease spread control program module 410 transmits a notification to the user that includes a suggestion to alter the user's actions to mitigate contagion spread. In another example, if the disease spread control program module 410 determines at step 520 that the facial and body movement state indicates that that the person is about to touch a surface such as a doorknob or light switch, then the disease spread control program module 410 sends a voice-based alert reminding the sick person to wash or sanitize his or her hands before touching the surface.

Still referring to FIG. 5, at step 530, the computer server 405 determines whether or not a sick person undertook a germ-transmitting activity. In embodiments, the disease spread control program module 410 determines whether or not a sick person undertook a germ-transmitting activity. In particular, for each person having a health status of sick (as determined at step 505), the disease spread control program module 410 receives digital still images and/or digital video of the person from the at least one camera 440. In embodiments, the disease spread control program module 410 analyzes the received digital still images and/or digital video using computer vision techniques and convolutional neural networks to determine an updated facial and body movement state for the sick person.

Still referring to step 530, in embodiments, the disease spread control program module 410 uses the updated facial and body movement state for the sick person to determine if the sick person undertook a germ-transmitting activity such as sneezing/coughing, touching a surface such as a doorknob or light switch, or undertaking any other germ-transmitting activity. In an example, the disease spread control program module 410 determines movements of facial muscles and/or body movements that indicate that the sick person is sneezing/coughing and/or that the sick person is touching a surface such as a doorknob or light switch.

Still referring to step 530, if the disease spread control program module 410 determines that the sick person undertook a germ-transmitting activity, then the flow proceeds to step 535. On the other hand, if the disease spread control program module 410 determines that the sick person did not undertake a germ-transmitting activity, then the flow returns to step 500.

Still referring to FIG. 5, at step 535, the computer server 405 determines a contaminated area. In embodiments, the disease spread control program module 410 determines an area that is contaminated from the germ-transmitting activity from step 530. In particular, the disease spread control program module 410 receives and analyzes images from the at least one camera 440 using computer vision techniques and convolutional neural networks to identify, as the contaminated area, physical objects affected by the germ-transmitting activity.

Still referring to step 535, in embodiments, the disease spread control program module 410 analyzes digital still images and/or digital video from the at least one camera 440 using computer vision techniques and convolutional neural networks to determine if another person is about to touch a contaminated area. In embodiments, if another person is about to touch a contaminated area, the disease spread control program module 410 sends a voice-based alert to the person via the at least one speaker 445. In embodiments, the voice-based alert is a reminder to the person to avoid touching the contaminated area or to wash hands after touching the contaminated area.

Still referring to step 535, in an example, the disease spread control program module 410 identifies a doorknob and light switch that were touched by a sick person as physical objects affected by the germ-transmitting activity. In another example, the disease spread control program module 410 analyzes images from the at least one camera 440 as well as climactic and/or other environmental conditions (e.g., temperature, air humidity, illumination, etc.) in the home, office, or other enclosed environment as determined using sensor data from one or more of the IoT sensors 435-1, 435-2, . . . , 435-*m* of the IoT devices 430-1, 430-2, . . . , 430-*m* to determine a size and path of clumps of respiratory droplets generated by a sick person (e.g., by sneezing/coughing) and a duration over which the clumps persist, and identify, as the contaminated area, physical objects affected by the clumps of respiratory droplets as well as a time duration over which the physical objects are affected.

Still referring to FIG. 5, at step 540, the computer server 405 determines germ-reduction abilities of the at least one cleaning robot 450. In embodiments, the disease spread control program module 410 determines the germ-reduction abilities of the at least one cleaning robot 450 by querying the at least one cleaning robot 450 or by retrieving information about the germ-reduction abilities of the at least one cleaning robot 450 from the cloud database 415. (In embodiments, the at least one cleaning robot 450 pre-registers its capabilities with the cloud database 415, using the disease spread control program module 410.) In an example, the disease spread control program module 410 determines, for each of the at least one cleaning robot 450, one or more surface types (e.g., hard surface floors, carpeted floors, walls, countertops, plumbing fixtures, textiles, etc.) that the cleaning robot 450 is capable of cleaning (i.e., reducing germs thereon).

Still referring to FIG. 5, at step 545, the computer server 405 activates at least one cleaning robot 450 to clean the contaminated area. In embodiments, the disease spread control program module 410 selects and activates at least one cleaning robot 450 having germ-reduction abilities (as determined at step 540) that correspond to the contaminated area (as determined at step 535). In an example, if the contaminated area determined at step 535 is a hard surface floor, then the disease spread control program module 410 selects at least one cleaning robot 450 that has germ-reduction abilities with respect to hard surface floors, such as a robot that is able to wet mop the floor. The activated at least one cleaning robot 450 is dispatched (deployed) by the disease spread control program module 410 to clean the contaminated area.

Still referring to step 545, in embodiments, the disease spread control program module 410 determines and manages a sterilization strategy based on predicted and/or actual disease spread. The disease spread control program module 410 then selects and activates at least one cleaning robot 450 having germ-reduction abilities in accordance with the sterilization strategy. In particular, the disease spread control program module 410 predicts disease spread based on correlation establishment and environment as follows: (1) The disease spread control program module 410 feeds a current health level matrix into a neural network of the disease spread control program module 410. (2) The neural network of the disease spread control program module 410, which includes internal layers with trained weights, calculates output values. (3) The neural network of the disease spread control program module 410 outputs a new matrix with difference in health levels for time (n+1). (4) The disease spread control program module 410 sets aside the time (n+1) results for later use. (5) The disease spread control program module 410 feeds these same results back into the neural network to create results for time (n+2). (6) The disease spread control program module 410 iteratively builds a projection of health level variation (disease spread) with similar external conditions and area coverage metric (for evaluating droplet contours). (7) The disease spread control program module 410 determines the sterilization strategy based on the projected disease spread. In an example, the sterilization strategy includes increasing cleaning cycles to sterilize surfaces in accordance with an area or time of predicted disease spread.

Still referring to FIG. 5, at step 550, the computer server 405 adjusts environmental conditions to minimize disease spread. In embodiments, the disease spread control program module 410 determines climactic conditions (e.g., temperature, air humidity, illumination, etc.) in the home, office, or other enclosed environment based on readings from one or more of the IoT sensors 435-1, 435-2, . . . , 435-m in one or more of the IoT devices 430-1, 430-2, . . . , 430-m. The disease spread control program module 410 then adjusts the climactic conditions (and/or other environmental conditions) in the home, office, or other enclosed environment to minimize disease spread in accordance with the sterilization strategy determined at step 545. In particular, in embodiments, the disease spread control program module 410 sends commands to one or more of the IoT devices 430-1, 430-2, . . . , 430-m to adjust the temperature, humidity level, and/or other environmental conditions in the home, office, or other enclosed environment to make conditions less favorable for disease spread. In an example, the disease spread control program module 410 sends commands to one or more of the IoT devices 430-1, 430-2, . . . , 430-m to raise a temperature and/or lower a humidity level in the home, office, or other enclosed environment to minimize disease spread. In another example, the disease spread control program module 410 adjusts the ventilation system to open or close vents to minimize disease spread.

Still referring to step 550, in embodiments, the disease spread control program module 410 uses machine learning to identify how viral diseases and other diseases spread and how climactic conditions and/or other environmental conditions contribute to disease spread. In embodiments, the disease spread control program module 410 adjusts the climactic conditions based on parameters that, via machine learning, are determined to make conditions less favorable for disease spread. Additionally, in embodiments, the disease spread control program module 410 sends a voice-based alert via the at least one speaker 445 to one or more persons in the home, office, or other enclosed environment, advising how to avoid disease spread (e.g., avoid the contaminated areas determined at step 535, wash hands, obtain sufficient sleep, etc.). The flow then returns to step 500.

In embodiments, the disease spread control program module 410 performs visual analysis using computer vision techniques. In particular, in embodiments, the disease spread control program module 410 uses a recurrent neural network such as bi-directional long short-term memory merged with a convolutional neural network for health detection and activity monitoring (e.g., at steps 505, 515, 520, and 530) in order to study a person's responses over period of time. Additionally, in embodiments, a person's patterns are studied with biometric information and correlated with health parameters of other persons in the vicinity. In embodiments, in determining the contaminated areas in step 535, directional vectors in computer vision (e.g., using Open CV in Python®, a registered trademark of the Python Software Foundation) are used to compute the average distance to other persons in the vicinity and at the same time, detect other objects in proximity with contamination risk thresholds (e.g., higher contamination risk for more proximal regions and lower contamination risk for far away objects).

In embodiments, the disease spread control program module 410 determines the health status of each person at step 505 using biometric information and correlation with health parameters of other persons in the vicinity. In particular, in embodiments, the disease spread control program module 410 trains a model used to determine the current and predicted health status of each person as follows: (1) Initially, each and every IoT sensor 435-1, 435-2, . . . , 435-m of the plurality of IoT devices 430-1, 430-2, . . . , 430-m forming an IoT sensor network, along with IoT cameras such as the at least one camera 440, continuously capture data. Based on sensor data analysis using artificial intelligence techniques, the disease spread control program module 410 learns different types of anomalies and health patterns of each person. (2) The disease spread control program module 410 uniquely identifies each and every person in the home, office, or other enclosed environment via a cloud identifier that is stored in the cloud database 415. (3) The disease spread control program module 410, using data received from the IoT sensors 435-1, 435-2, . . . , 435-m, determines health metrics as a percentage of threshold risk. (4) The disease spread control program module 410 converts health metrics and current health levels to a numerical format ranging from 1 to 5 (1 being healthy and 5 being a worsened condition including a cold and/or cough) for a time n and feeds them to a neural network. (5) The disease spread control program module 410 compares neural network output to initial health data for time n+1. (6) The disease spread control program module 410 adjusts weights as the neural network is trained over multiple sets of health parameters. (7) The disease spread control program module 410 uses temperature data and humidity level data from one or more of the IoT sensors 435-1, 435-2, . . . , 435-m along with other factors including sneezing locations determined using a convolutional neural network inculcated with the current training model.

Additionally, in embodiments, the disease spread control program module 410 determines current health conditions in a sustained geospatial environment and area being monitored as follows: (1) The disease spread control program module 410 iteratively collects data from the IoT sensors

435-1, 435-2, . . . , 435-m over a next time frame, and a health level is determined. (2) The disease spread control program module 410 inserts a current health level in the remaining matrix and the difference is computed from time interval n.

Additionally, in embodiments, the disease spread control program module 410 predicts future health conditions based on correlation establishment and environment as follows: (1) The disease spread control program module 410 feeds a current health level matrix into a neural network of the disease spread control program module 410. (2) The neural network of the disease spread control program module 410, which includes internal layers with trained weights, calculates output values. (3) The neural network of the disease spread control program module 410 outputs a new matrix with difference in health levels for time (n+1). (4) The disease spread control program module 410 sets aside the time (n+1) results for later use. (5) The disease spread control program module 410 feeds these same results back into the neural network to create results for time (n+2). (6) The disease spread control program module 410 iteratively builds a projection of health level variation with similar external conditions and area coverage metric (for evaluating droplet contours). (7) The disease spread control program module 410 determines maintenance plans based on projected time of health output state reaching a threshold risk for creating a quarantine condition in the home, office, or other enclosed environment, and/or notifies persons therein to take appropriate actions. (8) The disease spread control program module 410 communicates information to respective persons in the vicinity via known communication channels (e.g., the at least one speaker 445) stored in the cloud database 415.

In embodiments, a system and method identify when a user is sick; and in response to identifying that a user is sick, adjust one or more devices of the user to perform in a manner designed to mitigate spread of sickness associated with the user. Additionally, in embodiments, the system and method deploy one or more other devices of the user to sterilize potentially infected areas using a region-based convolutional neural network, and health metrics to initiate sterilization of areas determined to be potentially infected. Additionally, in embodiments, the system and method recommend actions a user can take to mitigate spread of sickness based on a predicted speed of propagation.

Additionally, in embodiments, the system and method identify when a user is sick based on a historical analysis of health-related data, medical information, and visual data analysis. Additionally, in embodiments, the adjusting one or more devices of the user to perform in a manner designed to mitigate spread of sickness associated with the user comprises: identifying a potentially contaminated area based on user interaction with the area; determining a level of contamination based on the user interaction; and deploying one or more other devices of the user to sterilize the area.

In embodiments, a service provider could offer to perform the processes described herein. In this case, the service provider can create, maintain, deploy, support, etc., the computer infrastructure that performs the process steps of the invention for one or more customers. These customers may be, for example, any business that uses cloud computing technology. In return, the service provider can receive payment from the customer(s) under a subscription and/or fee agreement and/or the service provider can receive payment from the sale of advertising content to one or more third parties.

In still additional embodiments, the invention provides a computer-implemented method, via a network. In this case, a computer infrastructure, such as computer system/server 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system/server 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   obtaining, by a computing device, information of a person from one or more remote wearable devices of the person via a computer network;
   determining, by the computing device, a health status of the person by analyzing the information of the person;
   determining, by the computing device, that the person is sick based on the health status;
   in response to determining that the person is sick, obtaining digital images of the person from a camera via the computer network;
   determining, by the computing device, body movements of the person determined to be sick by analyzing the digital images;
   determining, by the computing device, that the person determined to be sick performed a germ-transmitting activity based on the body movements; and
   deploying, by the computing device, a remote cleaning robot to clean a potentially contaminated area based on the determining that the person determined to be sick performed the germ-transmitting activity.

2. The computer-implemented method according to claim 1, wherein the information includes data from the one or more remote wearable devices of the person.

3. The computer-implemented method according to claim 2, wherein the determining the health status of the person is further based on historic information for the person.

4. The computer-implemented method according to claim 1, further comprising
   notifying, by the computing device, the person determined to be sick of an action to take to avoid the germ-transmitting activity.

5. The computer-implemented method according to claim 4, wherein the notifying the person determined to be sick of the action to take comprises the computing device triggering a voice-based alert.

6. The computer-implemented method according to claim 1, further comprising:

determining, by the computing device, the potentially contaminated area affected by the germ-transmitting activity.

7. The computer-implemented method according to claim 1, further comprising automatically adjusting, by the computing device, at least one environmental condition of an enclosed environment to minimize disease spread by sending a command to one or more devices to adjust the at least one environmental condition, wherein the at least one environmental condition is selected from the group consisting of: temperature; air humidity; and illumination.

8. A computer program product comprising a computer readable storage medium having program instructions embodied therewith, the program instructions executable by a computing device to cause the computing device to:
  obtain information of a plurality of persons from remote wearable devices of the plurality of persons via a computer network;
  determine a health status of each of the plurality of persons in an enclosed area by analyzing the information of the plurality of persons;
  determine that at least one of the plurality of persons is sick based on the health status;
  in response to determining that the at least one of the plurality of persons is sick, obtaining digital images of the at least one of the plurality of persons from a camera via the computer network;
  determine body movements of the at least one of the plurality of persons determined to be sick by analyzing the digital images using computer vision;
  determine that the at least one of the plurality of persons determined to be sick performed a germ-transmitting activity based on the body movements; and
  deploy a remote cleaning robot to clean a potentially contaminated area based on the determining that the at least one of the plurality of persons determined to be sick performed the germ-transmitting activity.

9. The computer program product according to claim 8, wherein the information includes data from the remote wearable devices of the plurality of persons selected from the group consisting of: heartrate data and temperature data.

10. The computer program product according to claim 9, wherein the determining the health status of each of the plurality of persons is further based on historic information for the plurality of persons.

11. The computer program product according to claim 8, the program instructions further being executable by the computing device to
  notify the at least one of the plurality of persons determined to be sick of an action to take to avoid the germ-transmitting activity.

12. The computer program product according to claim 11, wherein the notifying the at least one of the plurality of persons determined to be sick of the action to take comprises the computing device triggering a voice-based alert.

13. The computer program product according to claim 8, the program instructions further being executable by the computing device to cause the computing device to determine the potentially contaminated area affected by the germ-transmitting activity.

14. The computer program product according to claim 8, the program instructions further being executable by the computing device to cause the computing device to automatically adjust at least one environmental condition to minimize disease spread by sending a command to one or more devices to adjust the at least one environmental condition.

15. A system comprising:
  a hardware processor, a computer readable memory, and a computer readable storage medium associated with a computing device;
  program instructions to obtain information of a person from one or more remote wearable devices of the person via a computer network;
  program instructions to determine a health status of the person by analyzing the information of the person;
  program instructions to determine that the person is sick based on the health status;
  program instructions to obtain digital images of the person from a camera via the computer network in response to the determining that the person is sick;
  program instructions to determine body movements of the person determined to be sick by analyzing the digital images;
  program instructions to determine that the person determined to be sick performed a germ-transmitting activity based on the body movements; and
  program instructions to deploy a remote cleaning robot to clean a potentially contaminated area based on the determining that the person determined to be sick performed the germ-transmitting activity,
  wherein the program instructions are stored on the computer readable storage medium for execution by the hardware processor via the computer readable memory.

16. The system according to claim 15, wherein the information includes sensor data.

17. The system according to claim 16, wherein the determining the health status of the person is further based on historic information for the person.

18. The system according to claim 15, further comprising program instructions to notify the person determined to be sick of an action to take to avoid the germ-transmitting activity.

19. The system according to claim 18, wherein the notifying the person determined to be sick of the action to take comprises the computing device triggering a voice-based alert.

20. The system according to claim 15, further comprising:
  program instructions to determine the potentially contaminated area by determining a size and path of clumps of respiratory droplets generated by the person by analyzing the digital images.

* * * * *